United States Patent
Törmäläet al.

(10) Patent No.: US 6,692,497 B1
(45) Date of Patent: Feb. 17, 2004

(54) BIOABSORBABLE, DEFORMABLE FIXATION PLATE

(76) Inventors: Pertti Törmälä, Nestori Sarrin katu 1, 33720 Tampere (FI); Timo Pohjonen, Nosturinraitti 2 B 17, 33720 Tampere (FI); Harri Happonen, Ahkionkatu 16 B 5, 33850 Tampere (FI); Auvo Kaikkonen, Ojustenkatu 5 F 11, 33270 Tampere (FI)

(*) Notice: Subject to any disclaimer, the term of this patent is extended or adjusted under 35 U.S.C. 154(b) by 313 days.

(21) Appl. No.: 09/684,750

(22) Filed: Oct. 6, 2000

Related U.S. Application Data

(62) Division of application No. 09/036,259, filed on Mar. 6, 1998, now Pat. No. 6,221,075.

(51) Int. Cl.$^7$ ................................ A61B 17/80
(52) U.S. Cl. .......................... 606/69; 606/77
(58) Field of Search ............... 606/60, 61, 69, 606/70, 71, 72, 73, 75, 76, 77

(56) References Cited

U.S. PATENT DOCUMENTS

| | | |
|---|---|---|
| 4,671,280 A | 6/1987 | Dorband et al. |
| 4,871,256 A | 10/1989 | Grindon |
| 4,898,186 A | 2/1990 | Ikada et al. |
| 4,968,317 A | 11/1990 | Törmäläet al. |
| 5,227,412 A | 7/1993 | Hyon et al. |
| 5,290,281 A | 3/1994 | Tschakaloff |
| 5,324,307 A | 6/1994 | Jarrett et al. |
| 5,342,395 A | 8/1994 | Jarrett et al. |
| 5,485,713 A | 1/1996 | Moncrief |
| 5,569,250 A | 10/1996 | Sarver et al. |
| 5,589,942 A | 12/1996 | Gordon |
| 5,615,003 A | 3/1997 | Hermary et al. |
| 5,680,216 A | 10/1997 | Hierholzer et al. |
| 5,784,098 A | 7/1998 | Shoji et al. |
| 5,863,297 A | 1/1999 | Walter et al. |

FOREIGN PATENT DOCUMENTS

| | | |
|---|---|---|
| EP | 146398 | 6/1985 |
| EP | 0 491 983 | 7/1992 |
| EP | 0 449 867 B1 | 4/1994 |
| EP | 0321176 B1 | 2/1995 |
| FI | 88111 | 3/1989 |
| FI | 98136 | 9/1995 |
| FR | 2741255 | 11/1995 |
| WO | WO 90/04982 | 5/1990 |
| WO | WO 9007304 | 7/1990 |
| WO | WO 9012550 | 11/1990 |
| WO | WO 96/21638 | 7/1996 |
| WO | WO 9641596 | 12/1996 |
| WO | WO 97/11725 | 4/1997 |

OTHER PUBLICATIONS

F. Séquin and R. Texhammer, AO/ASIF Instrumentation, Springer–Verlag, Berlin, Heidelberg, 1981, pp. 21–22, 55–79, 107–108, 117–122.

L.–E. Moberg et al. Int. J. Oral. Maxillofac. Surg. 18 (1989) at pp. 311–314.

P. Paavolianen et al., Clin Orthop. Rel. Res. 136 (1978) pp. 287–293.

K. Lin et al., Plast. Reconstru. Surg. 87 (1991) pp. 229–235.

J. Fearon et al., Plast. Reconstr. Surg. 4 (1995) pp. 634–637.

C. Lindqvist, Brit. J. Oral Maxillofac. Surg. 33 (1995) pp. 69–70.

W. Muhlbauer et al., Clin. Plast. Surg. 14 (1987) pp. 101–111.

(List continued on next page.)

*Primary Examiner*—David O. Reip
(74) *Attorney, Agent, or Firm*—Kenyon & Kenyon

(57) ABSTRACT

The present invention relates generally to body tissue fixation systems, including body tissue fixation hardware comprising biocompatible, bioabsorbable (resorbable) thermoplastic plates, and methods of using those systems and hardware.

14 Claims, 8 Drawing Sheets

OTHER PUBLICATIONS

A. Sadove and B. Eppleg. Ann. Plast. Surg. 27 (1991) pp. 36–43.

R. Suuronen, Biodegradable Self–reinforced Polylactide Plates and Screws in the Fixation of Osteotomies in the Mandible, Doctoral Thesis, Helsinki University, Helsinki, 1992, pp. 16–18.

Eitenmüller et al., European Congress on Biomaterials, Abstracts, Instituto Rizzoli, Bologna, 1986, pp. 94.

K. Bessho et al., J. Oral. Maxillofac. Surg. 55 (1997) pp. 941–945.

G. Heimke et al. Biomaterials and Clinical Applications, Proc. of the Sixth Europ. Conf. On Biomaterials, Bologna, Italy, Sep. 14–17 (1986) pp. 92–104.

S. Vainionpää et al., Prog. Polym. Sci., 14 (1989) pp. 679–716.

S.I. Ertel et al., J. Biomed. Mater. Res., 28 (1995) pp. 919–930.

F.H. Silver et al., J. Long–Term Effects Med. Implants 1 (1992) 329–346.

N. Inoue, in Hydrostatic Extrusion, N. Inoue and M. Nishihara (eds.), Elsevier Applied Science Publishers, Barbing, England, 1985, pp. 333–362.

D.C. Tune and B. Jadhav, in Progress in Biomedical Polymers, eds. C.G. Gebelein R.L. Dunn, Plenum Press, New York 1992, pp. 239–248.

A.U. Daniels et al., Trans. Soc. Biomater. 12 (1989) 235.

A.U. Daniels et al. Trans. Soc. Biomater. 12 (1989) 74.

International Search Report for PCT/EP99/01438■.

International Preliminary Examination Report for PCT/EP99/01438■.

Gerlach et al., Biomaterials and Clinical Applications, Sep. 14–17, 1986, pp. 439 and 459■.

BIOABSORBABLE, DEFORMABLE FIXATION PLATE

CROSS-REFERENCE TO RELATED APPLICATION

This application is a division of U.S. Ser. No. 09/036,259, filed Mar. 6, 1998 now U.S. Pat. No. 6,221,075.

FIELD OF THE INVENTION

The present invention relates generally to body tissue fixation systems, including body tissue fixation hardware comprising biocompatible, bioabsorbable (resorbable) thermoplastic plates, and methods of using those systems and hardware.

BACKGROUND OF THE INVENTION

Traditional orthopedic and traumatological fixation systems to facilitate bone fracture healing (osteosynthesis) typically employ metallic hardware, e.g., plates, screws, rods and the like, formed of biocompatible, corrosion resistant metals such as titanium and stainless steel. Typical metallic plates are described, e.g., in the book, F. Séquin and R. Texhammar, AO/ASIF Instrumentation, Springer-Verlag, Berlin, Heidelberg, 1981, at p. 21–22, 55–79, 107–108, 117–122, the entire discloser of which is incorporated herein by reference. While such systems are generally effective for their intended purposes, they possess a number of inherent shortcomings. For example, metal release to the surrounding tissues has been reported. See, e.g., L.-E. Moberg et al. Int. J. Oral. Maxillofac. Surg. 18 (1989) at pp. 311–314, the entire disclosure of which is incorporated herein by way of this reference. Other reported shortcomings include stress shielding, see P. Paavolainen et al., Clin Orthop. Rel. Res. 136 (1978) 287–293, the entire disclosure of which is incorporated herein by way of this reference, and growth restriction in young individuals, see K. Lin et al., Plast. Reconstr. Surg. 87 (1991) 229–235, the entire disclosure of which is likewise incorporated herein by way of this reference. In infants and young children, there is the risk that metallic plates and screws can sink into and below the cranial bone, as a consequence of skull bone growth, thereby threatening the brain. See, e.g., J. Fearon et al., Plast. Reconstr. Surg. 4 (1995) 634–637, the entire disclosure of which is incorporated herein by way of this reference. Therefore, it is generally recommended that non-functional implants should be eventually removed, at least in growing individuals. See C. Lindqvist, Brit. J. Oral Maxillofac. Surg. 33 (1995) p. 69–70, the entire disclosure of which is incorporated herein by way of this reference.

Especially in maxillofacial and in cranial surgery, metallic mini plates are popular for use. See e.g., W. Muhlbauer et al., Clin. Plast. Surg. 14 (1987) 101–111; A. Sadove and B. Eppleg. Ann. Plast. Surg. 27 (1991) 36–43; and R. Suuronen, Biodegradable Self-reinforced Polylactide Plates and Screws in the Fixation of Osteotomies in the Mandible, Doctoral Thesis, Helsinki University, Helsinki, 1992, p. 16, and references therein, the disclosures of which are incorporated herein by reference. Mini plates are small, thin, narrow plates, which have holes for screw fixation. They are typically located on bone, perpendicularly over the fracture to fix the bone mass, on both sides of the fracture to each other. Typical geometries of mini plates are described e.g. in U.S. Pat. No. 5,290,281 at FIGS. 6A–6F, the entire disclosure of which is incorporated herein by way of this reference.

The main advantage of metallic plates (like titanium, stainless steel and cobalt chrome molybdenum plates), is that they are strong, tough and ductile so that they can be deformed or shaped (e.g., bended) at room temperature in the operation room, either by hand or with special instruments, to a form corresponding to the surface topography of bone to be fixed. In this way, the plate can be fixed flush on the bone surface to which the plate is applied.

In light of the above shortcomings of metallic plates, however, bioabsorbable plates have been developed for fracture fixation. Longitudinal, six-hole plates were developed for orthopaedic animal studies. See Eitenmüller et al., European Congress on Biomaterials, Abstracts, Instituto Rizzoli, Bologna, 1986, p. 94, the entire disclosure of which is incorporated herein by this reference. However, because of their inadequate strength, some of the plates were broken in animal experiments involving fracture fixation.

A special advantage of bioabsorbable plates is that they can be provided with openings for the insertion therethrough of surgical fasteners (like screws), while allowing means to permit the formation of additional fastener openings therethrough during a surgical procedure at the surgeon's discretion, as has been described in European Patent specification EP 0 449 867 B1, the entire disclosure of which is incorporated herein by way of this reference.

The main disadvantage of prior art bioabsorbable plates is that they can be deformed (bended) permanently and safely only at elevated temperatures above their glass transition temperature ($T_g$), as has been described e.g. in EP 0.449 867 B1 and in U.S. Pat. No. 5,569,250, the entire disclosures of which are incorporated herein by way of this reference. Below their $T_g$, the prior art bioabsorbable plates are brittle and break easily when deformed. Only at temperatures above the $T_g$ does the molecular structure of prior art plates have enough mobility to allow shaping (e.g., bending) without the risk of breaking. Accordingly, U.S. Pat. No. 5,569,250 describes a biocompatible osteosynthesis plate that is capable of being used in a secured relationship over a plurality of adjacent bone portions. That biocompatible osteosynthesis plate includes an elongated section having a top face and a bottom face, at least one fastener opening disposed between the top face and the bottom face, and means disposed upon the elongated section to permit the formation of additional fastener openings therethrough, during a surgical procedure. The osteosynthesis plate is in a first thermochemical state in a first configuration and is capable of being converted to a second thermochemical state so that it may be deformed prior to fixation. The first thermochemical state is typically room temperature (operation room conditions) and the second thermochemical state is typically an elevated temperature above the $T_g$ of the polymer material (e.g., for polylactides between 50–60° C.). Accordingly, in order to shape the plates disclosed in U.S. Pat. No. 5,569,250, they must be changed from their first thermochemical state to the second thermochemical state by heating, and thereafter they must be changed again back to the first thermochemical state prior to fixation. Because the thermal conductivity of polymeric materials is poor, the conversion of material to a second temperature is a slow process. Therefore, the clinical use of plates of U.S. Pat. No. 5,569,250 is tedious, slow and complex, especially if the surgeon must shape the plate several times to make it fit exactly to the form of the bone to be fixed.

K. Bessho et al., J. Oral. Maxillofac. Surg. 55 (1997) 941–7945, the entire disclosure of which is incorporated herein by reference, described a bioabsorbable poly-L-lactide miniplate and screw system for osteosynthesis in oral and maxillofacial surgery. However, in order to shape the plates of that reference, they first must be heated by immersion in a hot sterilized physiologic salt solution or by the application of hot air until they become plastic, and only then can they be fitted to the surface of the bone.

EP 0 449 867 B1 describes a plate for fixation of a bone fracture, osteotomy, arthrodesis etc., said plate being intended to be fixed on bone at least with one fixation device, like a screw, rod, clamp or corresponding device, wherein the plate comprises at least two essentially superimposed plates to provide a multilayer plate construction. The individual plates of said multilayer plate construction are flexible, so as to permit a change of form of said multilayer plate construction to substantially assume the shape of the bone surface in the operation conditions by means of an external force, such as by hand and/or by bending instrument directed to said multilayer plate construction, whereby each individual plate assumes a position of its own with respect to other individual plates by differential motion along the respecitive surfaces of coinciding plates.

Although the said multilayer plate fits even the curved bone surface without heating of individual plates, the clinical use of multilayer plates is tedious, because the single plates easily slip in relation to each other before fixation. Additionally, the thickness of multilayer plate system easily becomes too thick for cranio maxillofacial applications, causing cosmetic disturbances and increased risks of foreign body reactions.

U.S. Pat. No. 4,671,280, the entire disclosure of which is incorporated herein by reference, describes the manufacturing of a fastener member or staple, by the winding of an oriented bioabsorbable polymeric filament around, a forming bar, which winding is carried out at a temperature below the glass transition temperature of the polymer. Ordinarily, winding will be done at ambient temperature. Because the oriented filament is quite stiff, the coils are bowed out slightly from the sides of the forming bar. Thus, the coils do not fully assume the desired fastener member (or staple) configuration until the filaments are heated, which will normally be done during the annealing step (see, e.g., U.S. Pat. No. 4,671,280; Column 5, first two paragraphs). Thus, while U.S. Pat. No. 4,671,280 may describe some bending of drawn filament at an ambient temperature, the bending does not give the desired configuration of the material until the filaments are additionally heated. The filaments are heated during the annealing step to a temperature above the glass transition temperature of the material (see also Example 1 of U.S. Pat. No. 4,617,280).

A need, therefore, exists for a bioabsorbable (bioresorbable or biodegradable) osteosynthesis device, like a plate, which is thin and substantially rigid and substantially deformable at a first thermochemical state, being also dimensionally stable before and after deformation (shaping) in the said first thermochemical state. A need also exists for a bioabsorbable (bioresobable or biodegradable) osteosynthesis plate, which is strong, tough, does not produce a substantial inflammatory response, and which plate can be deformed, yet dimensionally stable at temperatures below the glass transition temperature ($T_g$) of the material from which the device is made, to facilitate shaping. A need further exists for such a bioabsorbable (bioresorbable or biodegradable) osteosynthesis plate, which is strong, tough, does not produce a substantial inflamatory response, and which plate can be deformed, yet dimensionally stable at room temperature in operation room conditions, to facilitate the shaping of the plate. Likewise, a need exists for such a bioabsorbable (bioresorbable or biodegradable) osteosynthesis plate, which is strong, tough, does not produce a substantial inflammatory response, and which plate can be deformed, yet dimensionally stable in operation room conditions (in the first thermochemical state) to allow its fixation on bone without distortion of the configuration of the bone fragments to be fixed, and which shaped plate is also dimensionally stable at a second thermochemical, state, in tissue conditions, when fixed on bone surface to facilitate non-problematic bone fracture healing.

SUMMARY OF THE INVENTION

Prior art, U.S. Pat. No. 5,569,250, teaches that bioabsorbable polymeric fixation implants, like plates, should be manufactured of non-oriented material and that the implants are relatively rigid at a first thermochemical state and are relatively deformable only at a second thermochemical state (at elevated temperature) to which the implant is temporarily brought prior to implantation.

In this invention we have found, surprisingly, that brittle and/or relatively weak bioabsorbable thermoplastic polymers, copolymers, polymer alloys or composites with ceramic particulate fillers or fiber reinforcements, having $T_g$ of the material above human body temperature, which materials cannot be deformed at room temperature, can be transformed through uni- and/or biaxial orientation of the material in the solid state to materials which are deformable at room temperature. Accordingly, the present invention describes uni- and/or biaxially oriented, rigid and tough materials and implants, like plates, which can be deformed at a first thermochemical state, like at room temperature in operation room conditions, prior to implantation; and which implants retain their deformed (shaped) form well in the second thermochemical state at body, temperature in tissue conditions, when implanted on bone, so that they keep the fixed bone fragments essentially in the desired position to facilitate bone fracture healing.

It should be emphasized that the first thermochemical state can be any temperature below $T_g$ of the material down to the room temperature area, because the uni- and/or biaxially oriented materials retain their properties of being substantially deformable and substantially rigid at such temperatures. An advantage of the present invention is to provide a low profile uni- and/or biaxially oriented biocompatible implant of sufficient strength to be capable of effecting a secured relationship between a plurality of adjacent bone portions. Another advantage of the present invention is to provide an uni- and/or biaxially oriented biocompatible implant that is bioresorbable over a desired period of time while not generating a substantial inflammatory response. A further advantage of the present invention is to provide an uni- and/or biaxially oriented bioabsorbable and biocompatible implant, like a plate, that is relatively rigid at a first thermochemical state, but is also relatively deformable at said first thermochemical state prior to implantation.

A further advantage of the present invention is to provide an uni- and/or biaxially oriented bioabsorbable implant that is capable of being repeatedly deformed at the said first thermochemical state prior to implantation. Another advantage of the present invention is to provide an uni- and/or biaxially oriented biocompatible implant that can be easily and inexpensively manufactured with reduced internal stresses. A further advantage of the present invention is that it provides an uni and/or biaxially oriented biocompatible fixation device that is capable of securing another such uni- or biaxially oriented biocompatible implant device and one or more adjacent bone portions.

The present invention, moreover, in one form thereof, provides a low-profile uni- and/or biaxially oriented biocompatible osteosynthesis plate that is capable of being shaped to secure a plurality of adjacent bone portions. The osteosynthesis plate of the present invention includes an elongated section having a top face and a bottom face, which elongated section is capable of being shaped to traverse a fracture site or osteotomy site for subsequent fixation to adjacent bone portions. The uni- and/or biaxially oriented osteosynthesis plate further includes a plurality of fastener openings disposed between the top face and bottom face to allow the traverse of a plurality of surgical fasteners therethrough. The osteosynthesis plate further includes means disposed upon the elongated section to permit the formation of additional fastener openings therethrough during a surgical procedure, at the discretion of the surgeon. The osteosynthesis plate is relatively rigid at a first temperature and is deformable in three dimensions, yet dimensionally stable, at said first temperature. The osteosynthesis plate retains a deformed position at said first temperature in operation conditions, but can be subsequently returned to its original configuration by redeformation at said first temperature and said first thermochemical state. As such, the uni- and/or biaxially oriented osteosynthesis plate of the present invention may be repeatedly deformed and returned to its original configuration at said first temperature (first thermochemical state), in order to contour the osteosynthesis plate precisely to a desired configuration through successive iterations.

The present invention also includes bioresorbable fixation devices, or bone screws, that are capable of being inserted through fastener openings disposed within the uni- and/or biaxially oriented osteosynthesis plates of the present invention. As such, the present invention contemplates a bone stabilization device including an uni- and/or biaxially oriented bioresorbable osteosynthesis plate and bioresorbable surgical fastener.

The present invention also provides a method for forming a low-profile, uni- and/or biaxially oriented biocompatible osteosynthesis plate, including the steps of formation of a sheet stock, polymer orientation uni- and/or biaxially, formation of an uni- and/or biaxially oriented, osteosynthesis plate from oriented sheet stock, finishing, surface cleaning, sterilization and packaging.

The present invention is also directed to a method for enabling a secured relation between a plurality of adjacent bone portions, including the steps of providing a low-profile, uni- and/or biaxially oriented, biocompatible, osteosynthesis plate, positioning the uni- and/or biaxially oriented biocompatible osteosynthesis plate upon a plurality of adjacent bone portions, providing a plurality of surgical fasteners for enabling a fixed relation between the uni- and/or biaxially oriented osteosynthesis plate and at least one adjacent bone portion, positioning the plurality of surgical fasteners within a plurality of fastener openings upon the uni- and/or biaxially oriented osteosynthesis plate and securing the plurality of surgical fasteners into the adjacent bone portions.

Uni- and/or biaxial orientation of polymers or polymer composites with solid state deformation is a well known process in polymer science and technology. During orientation, polymer molecules or their segments tend to align with their long axis in the orientation direction. A description of molecular background of orientation of polymeric materials and of its physical characterization is given, e.g., in U.S. Pat. No. 4,968,317, the entire disclosure of which is incorporated herein by reference. The effects of orientation are most pronounced in partially crystalline polymers, but it is also possible to orient non-crystalline (amorphous) polymers, as has been described in PCT/FI96/00511; the entire disclosure of which is also incorporated herein by way of this reference.

BRIEF DESCRIPTION OF THE DRAWINGS

Other advantages of the present invention will become apparent to one skilled in the art upon reading the following specification and the following drawings.

DESCRIPTION OF THE PREFERRED EMBODIMENTS

Figure 1:
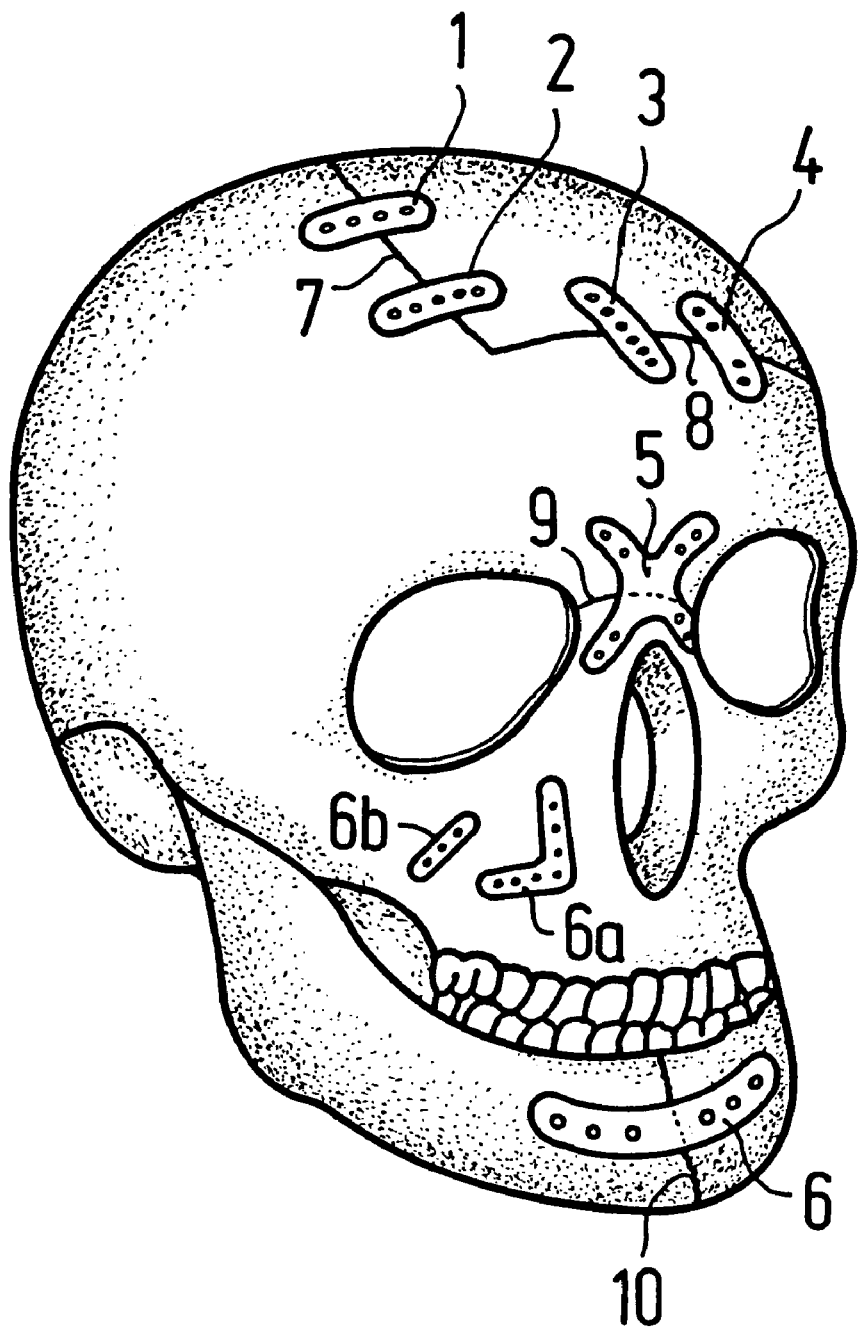
FIG. 1 describes a perspective view of a plurality of uni- and/or biaxially oriented osteosynthesis plates according to the present invention, shown in association with the repair of multiple cranio maxillofacial or mandibular fractures, or reconstruction to include pediatric and orthognatic areas.

For the purpose of promoting an understanding of the principles of the invention, reference will now be made to the preferred embodiments of the present invention. It will nevertheless be understood that no limitation of the scope of the invention is thereby intended, such alterations and further modifications, and such further applications of the principles of the invention therein being contemplated as would normally occur to one skilled in the art to which the invention relates.

Referring to FIG. 1A, there are shown uni- or biaxially oriented biocompatible, bioabsorbable osteosynthesis plates 1–6, 6a and 6b, according to preferred embodiments of the present invention. The uni- or biaxially oriented biocompatible osteosynthesis plates 1–6 are shown as being disposed over bone fractures 7–10, while plates 6a and 6b are shown as being disposed in position for facial reconstruction. It will be appreciated that the uni- or biaxially oriented biocompatible, bioabsorbable osteosynthesis plates of this invention like plates 1–6 (and 6a & 6b), may be of any size or shape as will be hereinafter discussed. Further, the uni- or biaxially oriented biocompatible osteosynthesis plates 1–6 (and 6a & 6b) may also be deformable and rigid at a first thermochemical state, like in operation room conditions. "A thermochemical state" as used in describing the present invention is defined according to U.S. Pat. No. 5,569,250, as a combination of thermal and chemical conditions resulting from exposure to certain thermal and chemical environments like room temperature and operation room atmosphere, respectively. Although one type of change in thermochemical state occurs by a change of temperature alone, changes in thermochemical state of an uni- and/or biaxially oriented biocompatible implant of the present invention should be understood as not limited only to changes in temperature. Preferably, the uni- and/or biaxially oriented biocompatible, bioabsorbable osteosynthesis plates of this invention are relatively rigid at both room temperature and at human body temperature and they are deformable at temperatures (like at room temperature) below the $T_g$ of the material from which the uni- and/or biaxially oriented biocompatible osteosynthesis plates are made. Therefore, there is no need to heat the plates of this invention to temperatures above the $T_g$ of the material, as must be done with prior art plates. Because of the uni- and/or biaxial molecular orientation of the materials of the invention, they exhibit the substantial rigidity and substantial deformability in all temperatures between $T_g$ of the material and room temperature or even to temperatures below room temperature.

Importantly, the uni- and/or biaxially oriented biocompatible, bioabsorbable osteosynthesis plates of this invention are formed by a method such that the uni- and/or biaxially oriented biocompatible osteosynthesis plates are dimensionally stable and deformable in operation conditions at room temperature and/or at any temperature above room temperature (first thermochemical state), but at or below body temperature (second thermochemical state). As used herein, the term dimensionally stable means that the uni- or biaxially oriented biocompatible, bioabsorbable osteosynthesis plates are able to retain substantially the same configuration at either of said two thermochemical states so that the uni- and/or biaxially oriented osteosynthesis plates facilitate bone fracture healing by keeping the fracture pieces in the proper position in relation to each other.

The rigidity, deformability and the dimensional stability of the plates are due to the manufacturing process of uni- and/or biaxially oriented plates, which is also discussed below. The uni- and/or biaxially oriented biocompatible osteosynthesis plates, like those of FIG. 1, are typically formed from uni- and/or biaxially oriented bioabsorbable polymer, copolymer, polymer alloy or composite with particle filler or fiber reinforcement. An example of such materials is a lactide (80 mol-%) and glycolide (20 mol-%) copolymer composition which is oriented and has a glass transition temperature of between 50° C. and 65° C.

Uni- and/or biaxially oriented osteosynthesis plates made using bioabsorbable oriented materials and in the manner discussed below will retain a substantial proportion of their strength after the first several weeks or months after implantation when this strength must be relatively high. Uni- and/or biaxially oriented osteosynthesis plates may be made of partially crystalline or non-crystalline (amorphous) materials. Uni- and/or biaxially oriented osteosynthesis plates of the invention are capable of stabilizing a plurality of bone portions for a period of from one to several months following implantation, and yet they will be completely resorbed after one year or several years following implantation, depending on such factors as chemical composition and molar mass of the bioabsorbable polymeric material, implant size and geometry or the position of the implant in the human body. Accordingly, the resorption time can be tailored to be fast or slow. Slow resorption is advantageous in the case of slow healing fractures and a relatively fast resorption of the bioabsorbable material reduces the unwanted cosmetic appearance as well as growth restriction in pediatric patients.

It will be appreciated that the uni- and/or biaxially oriented biocompatible, bioabsorbable osteosynthesis plate of the invention may be of a variety of sizes and/or shapes, as hereinafter discussed, and may also be of a bioresorbable material of different origins. In addition, the uni- and/or biaxially oriented biocompatible osteosynthesis plates are preferably both rigid and deformable at room temperature (below $T_g$ of the material) and at human body temperature.

Figure 2A:
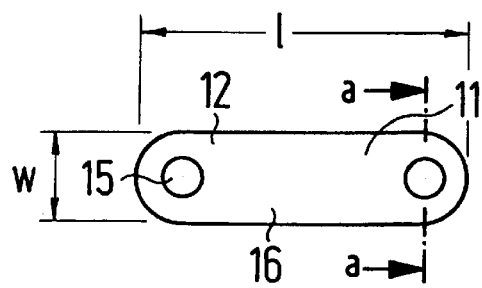
FIGS. 2A–2C describe stop views of osteosynthesis plates according to the teachings of some embodiments of the present invention.

Referring to FIGS. 2A–2D and 3, several uni- and/or biaxially oriented osteosynthesis plates according to the invention, are described. FIG. 2A shows a plate in the form of a flat plate 11. The flat plate 11 includes an elongated section 12 having a top face 13 and a bottom face 14. The flat plate 11 is further shown to include a plurality of fastener openings 15 that are of substantially cylindrical shape and are disposed between the top face 13 and the bottom face 14. The fastener openings 15 are operable to allow the traverse of surgical fasteners for enabling a secured relationship between the flat plate 11 and a bone surface (not shown) to which the flat plate 11 may be applied. It will be appreciated however, that the fastener openings 15 do not have to be present if there are other means for securing the flat plate 11 to bone. Preferably, the flat plate 11 is applied to a bone surface such that the plane or contour formed by the bottom face 14 is substantially flush with the bone surface to which the flat plate 11 is applied.

The flat plate 11 further includes means disposed upon the elongated section 12 to permit the formation of additional fastener openings therethrough at a plurality of different positions during a surgical procedure as was described, e.g., in EP 0 449 867 B1. In a typical embodiment, this is provided by having the elongated section 12 include a mid-portion 12a which is disposed between the fastener openings 15 and having substantially the same width as the portion of the flat plate 11, which is adjacent to the fastener openings 15. Accordingly, the surgeon is able to drill through the mid-portion 12a to form additional fastener openings as the particular application may require. It will be noted that additional fastener openings may be formed as well on, e.g., of the axis of the elongated section 12. It is natural that the arrangement of fastener openings and additional fastener openings can have different embodiments depending on the bone quality, fracture type etc. Other types of fastener opening and additional fastener opening combinations known in the art are shown in, e.g., in EP 0 449 867 B1.

Figure 3:
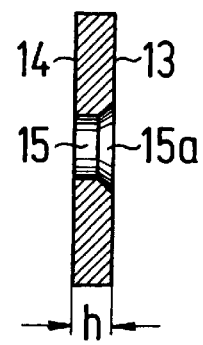
FIG. 3 is a cross-sectional view of an osteosynthesis plate of FIG. 2A along line a—a according to the teachings of a preferred embodiment of the present invention.

The flat plate 11 is has a "low profile" construction, that is, of a preferably thin nature so as to cause a minimum protrusion above the bone surface to which it is applied. In this regard, the term "low profile" will be used to refer to a construction in which the width is greater than about four to six times the height of the plate 11. For example, the plate 11 may typically have a width ("w") of 4–8 mm, a length ("l") of between about 10 mm to 80 mm and a height ("h") (thickness) of about 0.3 mm to 2 mm, as shown in FIGS. 2 and 3. The flat plate 11 is further provided to be preferably of a bioresorbable material, such that the flat plate 11 may be resorbed into the body through processes well known to those skilled in the art over a desired period of time. In this regard, the flat plate 11 may formed from one of the materials described in this invention.

The flat plate 11 is also characterized by its ability to be deformed, without heating it above the $T_g$ of the plate material, during, a surgical procedure where it will be conformed to the contour of the bone surface to which it is applied. This feature is especially useful in the surgical repair of bone surfaces having high curvatures, including the maxillofacial bones of the craniofacial skeleton. During such deformation, the flat plate 11 is deformed by manipulating the plate by hand or with manipulating device(s) in a first thermochemical state, i.e., in the operation room conditions during a surgical operation. Accordingly, there is no need, before its deformation, to elevate that plate to a higher temperature, using e.g., a heating device, as is needed in prior art U.S. Pat. No. 5,569,250. The deformed plate of the invention will then be placed into the second thermochemical state when fixed on bone in the, body to secure the bone fracture. More preferably, because the flat uni- and/or biaxially oriented osteosynthesis plate 11 is formed by a method which causes the plate to be deformable, ductile, rigid and dimensionally stable during operation under the operation room conditions, in the first thermochemical state, the flat plate 11 is able to return to its original configuration upon deforming it again in operation room conditions. As such, it will be appreciated that this ability allows the flat plate 11 to be repetitively deformed and returned to its original configuration, thus allowing for successive attempts by a surgeon during a surgical procedure to conform the flat plate 11 in three dimensions to correspond as closely as possible to the contours of the bone surface to which the flat plate 11 will be applied. These successive deformations can be done conveniently and rapidly in operation room by operation table without heating and cooling conversions, which are necessary for the bending of prior art plates, like those of U.S. Pat. No. 5,569,250.

The formation of additional fastener openings through the flat plate 11 may be accomplished by simply drilling through the material from which the flat plate 11 is made as discussed above. Such drilling is performed through means well known to those skilled in, the art. The flat plate 11 is then operable to accept a plurality of surgical fasteners, such as biocompatible and bioresorbable bone screws, which may be constructed of the same material as the flat plate 11, or may alternatively be made of another bioabsorbable material.

The positioning of the flat plate 11 is preferred to be with its bottom face 14 in substantially flush contact with the bone surface to which it is applied, and with a plurality of fasteners (not shown) disposed therethrough for securing it into position, wherein the head of the surgical fastener is tightened against the top face 13 of the flat plate 11. This arrangement results in a secured relationship between the flat plate 11 and the underlying bone surface. According to an advantageous embodiment, the fastener opening 15 (see FIGS. 2 and 3) is conically widened from its opening end on the top face 13 so that it forms a countersink 15a on the top face 13.

Figure 2B:
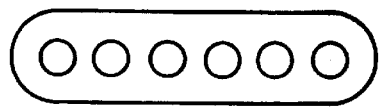
Figure 2C:
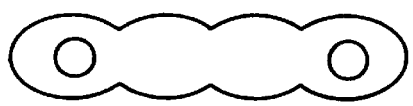
Figure 2D:
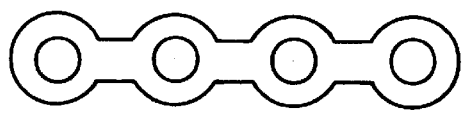

In addition to a simple plate with a constant width w and one or several fastener openings (as is seen in FIGS. 2A and 2B) the uni- or biaxially oriented, bioabsorbable plates of the invention can have such a design that the width of the plate in the area of the isthmus between two fastener openings is smaller than the width of plate around the fastener openings (or the width of the area into which additional fastening openings can be drilled). FIGS. 2C–2D describe such plates. A special advantage of plates of FIGS. 2C–2D is that these plates can be deformed also in the flat plane of the plate (in the plane of figure), in addition to bending and torsional deformations, which are typical for constant width plates, like those of FIGS. 2A–2B.

Figure 4:
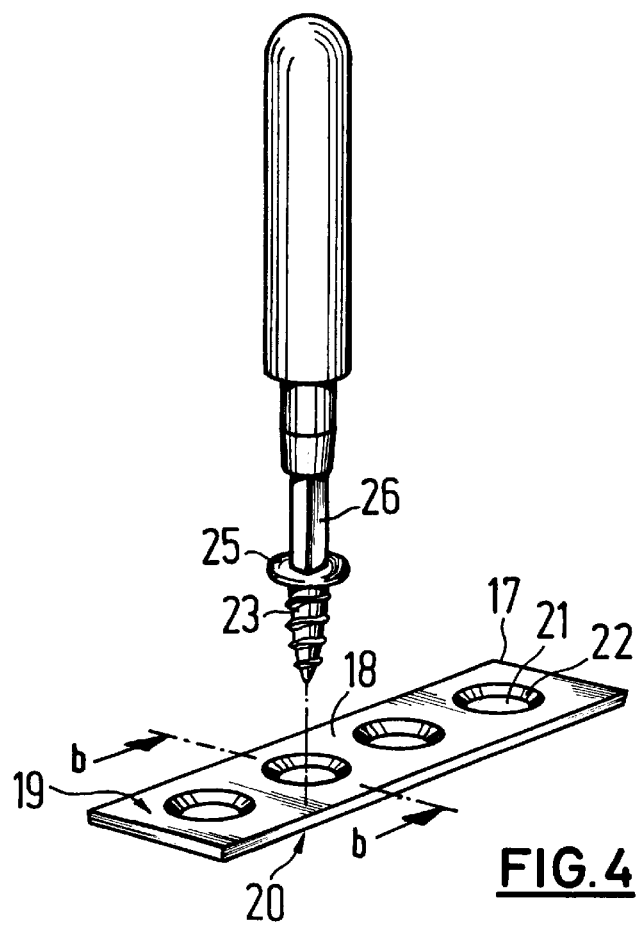
FIG. 4 is a perspective view illustrating an uni- and/or biaxially oriented osteosynthesis plate, in combination with a bone screw positioned in a relative elevated position for insertion within a fastener opening of the uni- or biaxially oriented osteosynthesis plate.
Figure 5:
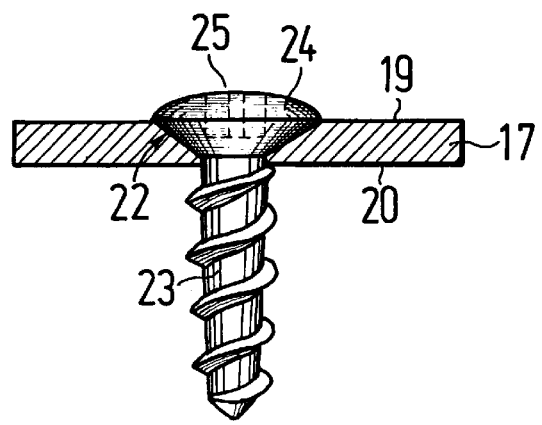
FIG. 5 is a cross-sectional view of the osteosynthesis plate shown in FIG. 4 along line b—b, with a bone screw disposed within a fastener opening of the osteosynthesis plate.

Referring now to FIGS. 4 and 5, there is shown a uni- or biaxially oriented biocompatible flat osteosynthesis plate 17 according to a preferred embodiment of the present invention. FIG. 4 illustrates a perspective view of the osteosynthesis plate 17, which includes an elongated section 18 having a top face 19 and a bottom face 20. The flat, smooth-surfaced configuration of osteosynthesis plate is intended to render the plate 17 in a "low-profile" configuration. This is accomplished by makeing the elongated section 18 to be as thin as possible to accomplish the desired result without any protrusions which disadvantageously increase the thickness of the plates according to the prior art U.S. Pat. No. 5,569,250. Preferably, the width of the osteosynthesis plate 17 is greater than approximately four to six times the thickness of the plate. It has been determined that a minimum thickness of the plate is desirable for minimizing the amount of mass and the cross-section of the osteosynthesis plate 17, as well as providing the desired resorption time for a complete resorption of the osteosynthesis plate into the body. It has also been determined that this principle, which involves the spreading of the mass of an osteosynthesis plate over a larger surface area, provides improved results in both reducing the cosmetic effect of implantation of these devices, as well as providing a more favorable time for resorption of the material due to smaller cross-sectional area.

The osteosynthesis plate 17 is also characterized by its ability to be deformed during a surgical procedure in the operation room conditions, to be conformed to the contour of the bone surface to which it is applied. This feature is especially useful in the surgical repair of bone surfaces having high curvatures, including the maxillofacial bones of the skull, as previously described.

The osteosynthesis plate 17 also includes a plurality of fastener openings 21 which are disposed between the top face 19 and the bottom face 20. As before, the fastener openings 21 are operable to allow the traverse of a plurality of surgical fasteners therethrough. The fastener openings 21 may each be further provided with a countersink 22 which is capable of acceping a preferably correspondingly shaped portion of a head of a surgical fastener. As such, the countersink 22 may be oriented in a substantially hemispherical configuration, sa a substantially frustoconical configuration, or in any other configuration suitable for the particular need.

FIGS. 4 and 5 also illustrate a surgical fastener in the form of a bone screw 23 located above the surface of the osteosynthesis plate 17 in FIG. 4, and located in its fully inserted position in FIG. 5. When fully inserted, the head 24 of the bone screw 23 may be mainly or substantially contained below the top face 19 of the plate 17 thereby complementing the low-profile configuration of the osteosynthesis plate 17. The bone screw 23 may be made from the same or different biocompatible and bioabsorbable material as the osteosynthesis plate 17, thereby providing a fully bioresorbable bone stabilization device.

As is illustrated in FIGS. 4 and 5, when the surgical fastener is provided in the form of a bioresorbable bone screw 23, head 24 of the bone screw 23 includes a fastener socket 25 into which the tip of the installation tool, like a screwdriver 26, can be pushed. The screwdriver 26 is used for engaging the bone screw 23 for insertion within a fastener opening 21 and subsequent rotation of the bone screw 23 while threading into an underlying bone structure. The cross-section of the socket 25 can be e.g., triangular, quadrangular (like in FIG. 4), hexagonal, etc. It will be appreciated that the socket 25 and the corresponding tip of a screwdriver 26 may be shaped in any suitable configuration to match each other.

Figure 6A:
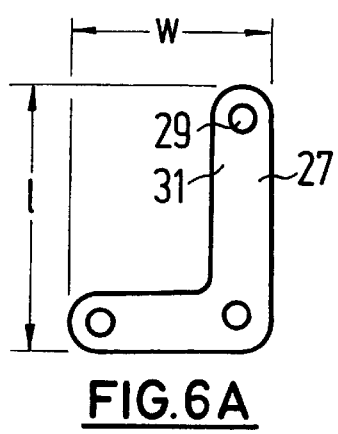
FIGS. 6A–6J describe as top views some other typical geometries of uni- and/or biaxially oriented osteosynthesis plates according to the teachings of the present invention.
Figure 6B:
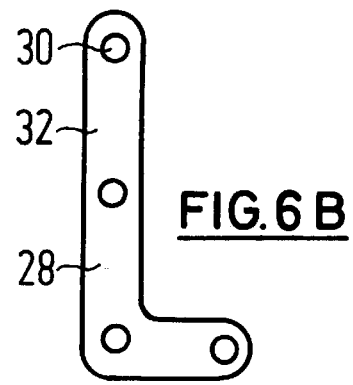
Figure 6C:
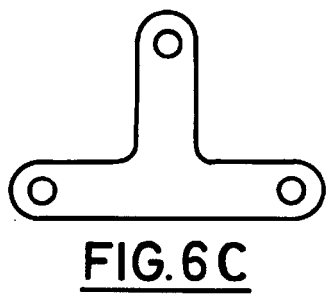
Figure 6D:
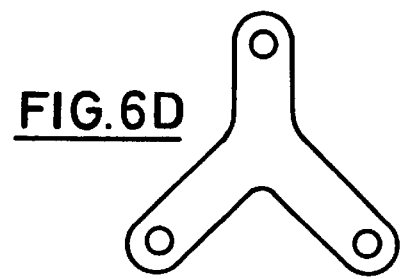
Figure 6E:
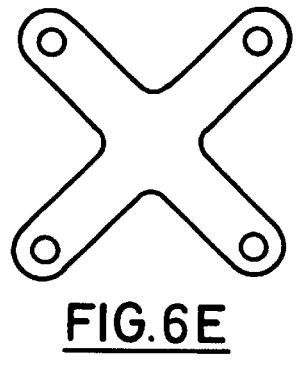
Figure 6F:
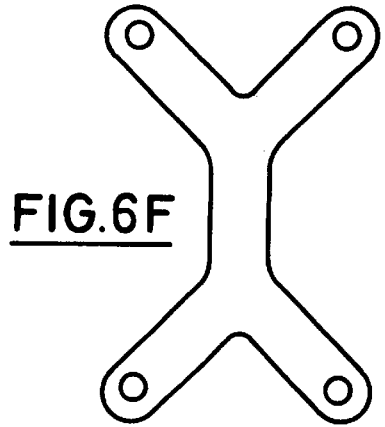
Figure 6G:
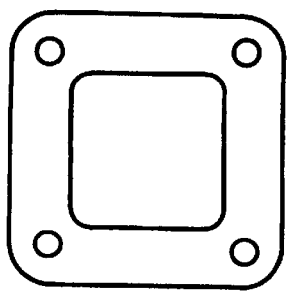
Figure 6H:
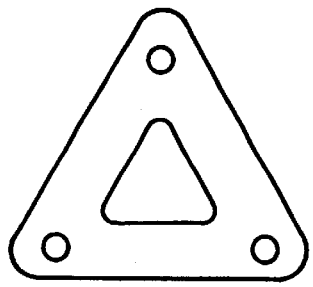
Figure 6:
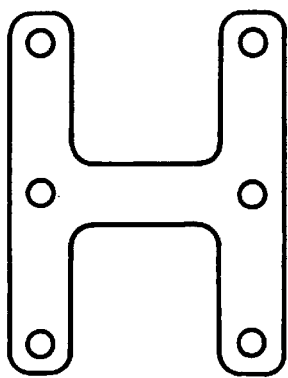
Figure 6:
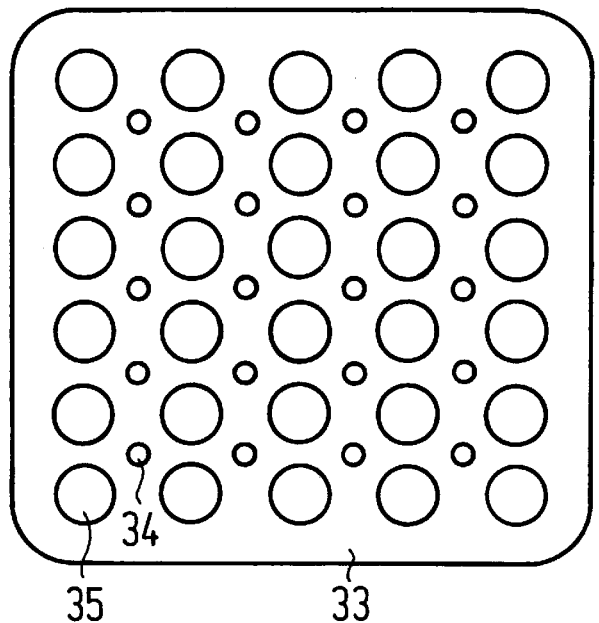

Referring to FIGS. 6A through 6J, there are shown a plurality of configurations of flat uni- or biaxially oriented osteosynthesis plates according to the present invention. FIGS. 6A and 6B show L-plates 27 and 28 according to the present invention. The L-plates 27 and 28 are further shown to include a plurality of fastener openings 29 and 30 disposed upon the elongted sections 31 and 32 near the terminal portions and at the corner sections of the elongated sections. A typical L-plate 27 has a width w of about 12 mm, a length (l) of a about 20 mm and a thickness of about 0.5–1.0 mm FIGS. 6C–6I show other configurations of plates, like a T-plate (6C), Y-plate (6D), X-plates. (6E and 6F), square plate (6G), triangle plate (6H) and H-plate (6I). All of such plates may include a plurality of holes for fasteners, depending on the size and use indications of the plate. FIG. 6J shows a mesh-plate 33 with a plurality of smaller holes 34 for fastener fixation and bigger holes 35 to facilitate tissue healing through the plate 33 and to reduce the mass of the plate 33. It will be appreciated that the examples set forth in FIGS. 6A–6J are meant to be only illustrative, and not a limitation, of the varieties of osteosynthesis plate shapes which may be constructed according to the present invention. It will further be appreciated that these osteosynthesis plates may be constructed of any of the materials previously discussed, or may be constructed from other suitable materials. As before, it is preferred that any of the above osteosynthesis plates be constructed of a bioabsorbable (resorbable) material. Also as before, the bioabsorbable material may be combined in a bone stabilization device with bioabsorbable surgical fasteners, such as bone screws.

It will also be appreciated that any of the above osteosynthesis plates may be constructed in a configuration, as shown in FIGS. 1–6. In addition, it will be appreciated that any of the above osteosynthesis plates may be constructed to include means disposed upon the elongated section to permit the formation of additional fastener openings therethrough during a surgical procedure, as provided in EP 0 449 867 B1, and in the description relating to FIGS. 2 and 3 herein. Further, all of the above-mentioned osteosynthesis plates are intended to be of a low-profile configuration, constructed in a flat configuration, such as in FIGS. 1–6.

The osteosynthesis plates of the present invention can be manufactured off thermoplastic bioabsorbable (resorbable or biodegradable) polymers, copolymers, polymer alloys, or composites e.g. of polyp-α-hydroxy acids and other aliphatic bioabsorbable polyesters, polyanhydrides, polyorthoesters, polyorganophosphatzenes, tyrosine polycarbonates and other bioabsorbable polymers disclosed in numerous publications, e.g. in S. Vainionpääet al., Prog. Polym. Sci., 14 (1989) 679–716, FI Patent No. 952884, FI Patent No. 955547 and WO-90/04982, EP 0449867 B1, U.S. Pat. No. 5;569,250, S. I. Ertel et al., J. Biomed. Mater, Res., 29 (1995) 1337–1348 as well as in the reference publications mentioned in the aforementioned publications, the disclosures of all of which are incorporated herein by way of this reference.

Implants in accordance with the invention can be manufactured of biodegradable polymers by using one polymer or a polymer alloy. The implants can also be reinforced by reinforcing the material by fibres manufactured of a resorbable polymer or of a polymer alloy, or with biodegradable glassfibres, such as β-tricalsiumphosphate fibres, bioglassfibres or CaM fibres (cf e.g. EP146398, the entire disclosure of which is incorporated herein by way of this reference). Ceramic powders can also be used as additives (fillers) in implants to promote new bone formation.

Implants according to the invention can also contain layered parts comprising a flexible outer layer, which is a surface layer improving the toughness of the implant and/or operating as a hydrolysis barrier, and a stiffer inner layer or core of the implant. To prepare such an embodiment, the implant can be coated with an outer layer having different chemical and mechanical properties (e.g., hydrolysis and strength retention) than the core of the implant. In such a case, an outer layer having greater resistance to hydroysis than the implant's core can be used, enabling the implant (after insertion in a patient) to retain its strength and biodegrade in less time than it would have without such an outer coating.

It is natural that the materials and implants of the invention can also contain various additives for facilitating the processability of the material (e.g. stabilizers, antioxidants or plasticizers) or for changing its properties (e.g. plasticizers or ceramic powder materials or biostable fibres, such as carbon) or for facilitating its treatment (e.g. colorants). According to one advantageous embodiment the implant of the invention contains some bioactive agent or agents, such an antibiotics chemotherapeutic agents, agents activating healing of wounds, growth factor(s), bone morphogenic protein(s), anticoagulant (such as heparin) etc. Such bioactive implants are particularly advantageous in clinical use, because they have, in addition to their mechanical effect, also biochemical, medical and other effects to facilitate tissue healing and/or regeneration.

A typical manufacturing procedure to make plates of the present invention is as follows. First the polymer raw material (and optional additives and/or filler(s) and/or reinforcing fibers) in the form of a powder, flakes, pellets or granulate, etc., will be melted in a continuous process, like extrusion, or with a noncontinuous process, like injection molding or compression molding. The melted material will be cooled so that it solidifies to an amorphous or partially crystalline (crystallinity typically 5–50%) preform, like a cylindrical rod or bar, a flat balk with a rectangular cross-section, a plate or a sheet stock. Cooling can be done inside a special mold in injection molding and in compression molding techniques. In extrusion, the preform will be formed from material melt in a die and the preform will be led onto a special cooling belt or into a cooling solution to make a solid preform. Thereafter, the solid preform will be oriented with, uni- and/or biaxial solid-state deformation process,to create an oriented plate preform. The orientation transforms the sheet stock, which cannot be deformed without substantial damage or breaking at room temperature, into a form where the molecular orientation toughens the sheet stock, so that after orientation it can be deformed without substantial damage or breaking at room temperature or also at any higher temperature between room temperature and Tg of the polymeric raw material.

The orientation is typically made at a temperature (T) above $T_g$ of the polymeric raw material, but below the melting temperature of the material, if it is partially crystalline. The orientation is typically made by drawing the unoriented plate preform in the solid state. The drawing can be done freely by fixing the ends of the plate preform into fixing clamps of a drawing machine, tempering the system to the desired drawing temperature and by increasing the distance between the fixing clamps so that the plate preform is stretched and oriented structurally. This type of orientation is mainly uniaxial. The drawing can be done also through a conical die, which can have, e.g., a circular, an ellipsoidal, a square or rectangular cross-section. When the cross-sectional area of the bioabsorbable polymer billet, which will be drawn through the die is bigger than the cross-sectional area of the die outlet, the billet will be deformed and uni- and/or biaxially oriented during the drawing, depending on the geometry of billet and die.

The billet may be forced through the die also by pushing the billet mechanically with a piston through the die (ram extrusion) or by pushing the billet through the die with hydrostatic pressure (see e.g. N. Inoue, in Hydrostatic Extrusion, N. Inoue and M. Nishihara (eds.), Elsevier Applied Science Publishers, Barbing, England, 1985, p. 333–362, the entire disclosure of which is incorporated herein by way of this reference).

Figure 7A:
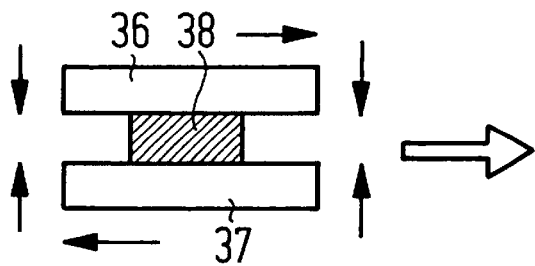
FIG. 7 is a cross-sectional view of plates showing deformation of a plate preform with a shear mode.
Figure 7B:
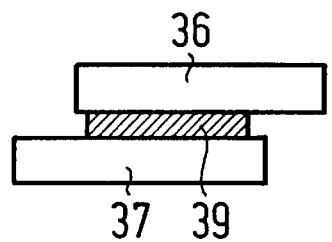

It is also possible to, create orientation by shearing the flat billet between two flat plates which glide in relation to each other and approach each other at the same time, as is seen schematically in cross-sectional FIGS. 7A and 7B, where 36 and 37 are shearing plates and 38 is a billet before shearing and 39 a billet after shearing. The arrows in FIG. 7A show the course of motion of shearing plates 36 and 37 in relation to each others.

It is also possible to deform the billet in a compression molding device between flat plates which are pushed towards each other, so that the billet deforms biaxially between the plates and attains the desired final thickness. The deformation can be done also by rolling the rod-like or plate-like preform between rollers, which flatten the preform to the desired thickness orienting the material at the same time biaxially. It is natural that different deformation methods can be combined with each other. For example, hydrostatic deformation can be combined with die drawing, or rolling can be combined with drawing, e.g., by using two pairs of rollers, one set after the other, which rollers have different rolling speeds, etc. Optionally, the billet and/or die, compression plates or rolls can be heated to the desired deformation temperature with electrical heating or with a suitable heating medium, like a gas or heating liquid. The heating can be done also with microwaves or ultrasonically to accelerate the heating of the billet.

Regardless of the deformation method, the purpose of the solid state deformation is the orientation of the material uni- and/or biaxially, so that the material is transformed to such material that is substantially rigid and substantially deformable at the conditions of surgical operation.

Solid state deformation, to create oriented bioabsorbable fixation materials, has been described in several publications, like in U.S. Pat. No. 4,671,280, U.S. Pat. No. 4,968,317, U.S. Pat. No. 4,898,186, EP 0 321176 B1, WO 97/11725, D. C. Tunc and B. Jadhav, in Progress in Biomedical Polymers, eds. C. G. Gebelein and R. L. Dunn, Plenum Press, New York 1992, p. 239–248, FI Patent No. 88111 and FI Patent No. 98136, the entire disclosures of each of which are incorporated herein by way of this reference. However, only in this invention have we found, surprisingly, that when the rigid bioabsorbable (resorbable) fixation plate material, which cannot be deformed substantially at temperatures below $T_g$ of the material, is oriented uni- and/or biaxially, it is transformed into a material which is substantially rigid but can be deformed substantially at temperatures below $T_g$ of the material, for use advantageously in bone fracture, fixation.

Following the orientation step, osteosynthesis plates, such as flat plates of FIGS. 1–6, can be formed from the oriented sheet stock by machining or stamping the plate and the fastener opening(s) and the countersink(s). The next step of the method of the present invention involves the finishing of the plates, to provide a smooth surface and an aesthetic appearance for the article. This is accomplished by trimming with suitable trimming devices, such as knives or cutting blades, or may also be accomplished by an additional stamping step. Once the removal of surface irregularities has occurred, the substantially completed product is subjected to cleaning with a suitable cleaning agent, like ethyl alcohol water mixture. Mechanical agitation and ultrasonic agitation can be used to facilitate the cleaning. In this step, the outer surface of the osteosynthesis plate is cleaned of fingerprints, soils and oils resulting from contact with human hands and other surfaces, as well as impurities which may collect on the surface.

In the next step of the method of the present invention the plates are dried in high vacuum, optionally at an elevated temperature, and packed into a plastic foil and/or aluminum foil pouch(es) which is (are) sealed. Another drying step and filling of the pouch with an inert gas (like nitrogen or argon gas) before heat sealing of the pouch, may also be carried out. In the next step the plates closed into the packages, are sterilized with γ-radiation, using a standard dose of radiation, (e.g., 2.5–3.5 MRad). If gas sterilization will be used (like ethylene oxide), the plates must be sterilized before closing the package It is natural that the above-mentioned steps of manufacturing an osteosynthesis plate of the present invention may further include additional steps, such as for quality control purposes. These additional steps may include visual or other types of inspections during or between the various enunciated steps as well as final product inspection including chemical and/or physical testing and characterization steps and other quality control testing.

The method for imparting a secured relationship between a plurality of adjacent bone portions according to the present invention will now be described. The first step of this method includes providing a, sterile, low-profile uni- or biaxially oriented biocompatible osteosynthesis plate, such as any of the osteosynthesis plates of FIGS. 1–6. This is achieved by opening the plate package in an operation room by an operation table and supplying the sterile plate to the surgeon. Depending on the surface topography of the bone to be fixed, the surgeon then shapes (deforms), if necessary, the osteosynthesis plate to a first desired configuration by hands or with any manipulation instrument. The surgeon can then test the result of shaping conveniently, by pressing the plate gently against the bone to be fixed, and if the first desired configuration is no, sufficient for completing the surgical requirements, the surgeon can reshape the osteosynthesis plate to a second desired configuration.

In addition, it will be appreciated that the method of the present invention further includes the capability for repetitively reshaping, at constant operation room temperature, the osteosynthesis plate to successive desired configurations and ceasing reshaping the osteosynthesis plate when a desired final configurations of the osteosynthesis plate has been archived.

The osteosynthesis plate is then positioned upon a plurality of adjacent bone portions. A plurality of surgical fasteners are then provided for imparting a fixed relationship between the osteosynthesis plate and at least one adjacent bone portion. A plurality of surgical fasteners are then positioned within a plurality of fastener openings located upon the osteosynthesis plate. The plurality of surgical fasteners are then secured to the adjacent bone portions, thereby engaging the low-profile biocompatible osteosynthesis plate with each bone portion. This method may further include the additional steps of creating at least one additional fastener opening through the osteosynthesis plate at a location adjacent to at least one bone portion, positioning an additional surgical fastener within each additional fastener opening, and securing each additional surgical fastener into each bone portion, thereby enhancing an engagement of the osteosynthesis plate with each bone portion, as was described e.g. in EP 0 449 867 B1. This method may also include the step of engaging the osteosynthesis plate with at least one adjacent osteosynthesis plate.

Alternatively, the method for imparting a secure relationship between a plurality of adjacent bone portions is similar to that described above, but the osteosynthesis plate is secured by means of an adhesive. In this regard, after the osteosynthesis plate is formed in the manner described above, the surgeon places an adhesive between the bone portions to be secured and the osteosynthesis plate. The adhesive may typically be a cyanoacrylate, though other suitable adhesives may be used. The surgeon then brings the osteosynthesis plate into contact with the bone portions, thereby securing the osteosynthesis plate to the bone, portions.

The principles of the present invention described broadly above will now be described with reference to the following specific examples without intending to restrict the scope of the present invention.

EXAMPLE 1

Pellets of copolymer material comprising about 80 mol-% of L-lactide and about 20 mol-% of glycolide were supplied by PURAC biochem bv, of Gorinchem, Holland. The pellets, were formed such that they had an inherent, viscosity of about 5.9 dl/g and a molecular weight Mv of about 336,000. The inherent viscosity was measured at 25° C. using 100 mg polymer per 100 ml of chloroform.

The pellets were extruded into a form of a cylindrical bar with a diameter of 6.0 mm using a single screw extruder (Axon BX-15, Axon Plastmaskiner, Sweden) and allowed to cool to ambient room temperature (20° C.). The extruded bar had an inherent viscosity of about 3.4 dl/g and a molecular weight Mv of about 158,000. The crystallinity of the extruded bar was about 1.5% and the glass transition temperature $T_g$ was about 53° C. (as measured with differential scanning calorimeter, Perkin-Elmer DSC-7). To induce crystallinity, the extruded bar was then annealed for 16 hours under vacuum (0.02 mbar) at 110° C. After annealing, the inherent viscosity of the bar was unchanged (about 3.4 dl/g) and the crystallinity was about 19%. The annealed bar was oriented uniaxially by drawing it through a heated tapered die (T=90° C.) to produce an oriented rod with a diameter of 3.0 mm (draw ratio=4). After orientation, the crystallinity of the material was over 20%.

The uniaxially, oriented rod was oriented biaxially by compressing it between parallel stainless steel molding plates. A steel band of the thickness of 1.2 mm was placed between the molding plates on both sides of the rod (these bands determined the thickness of the plate after molding). The rod was preheated three minutes at 60° C. under low compression force (~0.1 kN), which prevented shrinking while allowing the material to become rubbery. After preheating the temperature of the compression molding plates was elevated stepwise at 10° C. increments (during 3 minutes) to 90° C., while elevating also the compression force stepwise at 10 kN increments to 30 kN. The mold was then cooled rapidly (in 2 minutes) to room temperature (20° C.) with cooling water led into cooling channels in the walls of the mold. The mold was opened and the plate like biaxially oriented preform was removed from the mold. Such preforms were then processed further with drilling and grinding, producing plates having a configuration similar to the plate shown in FIG. 2B. The dimensions of the machined plates were 1.2×5.5×40 mm. The holes had a diameter of 1.5 mm and they were located at 3 mm distance from each other. The plates were then gamma sterilized with a minimum dose of 2.5 MRad (25 kGy). After gamma irradiation the inherent viscosity of the plates was about 1.3 dl/g and the molecular weight Mv was about 42,000. The crystallinity of the plates was determined to be more than 20%. A flexural strength of 180 MPa was measured for the plates.

Figure 8A:
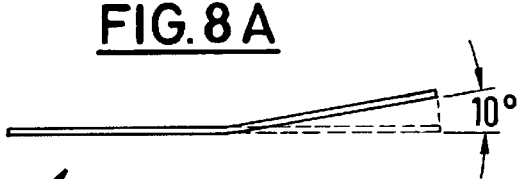
FIGS. 8A–8C show schematically the bending of plates of the invention at room temperature.
Figure 8B:
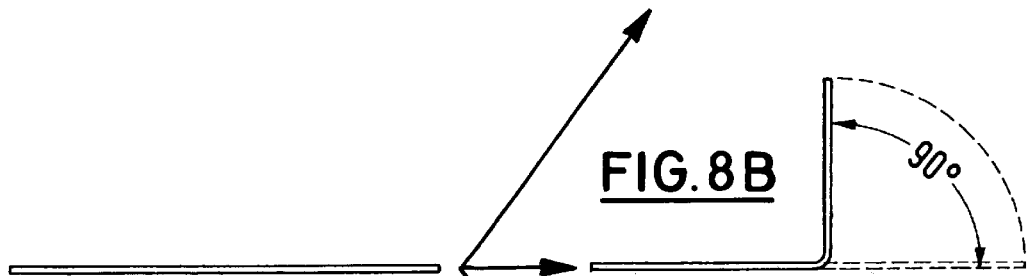
Figure 8C:
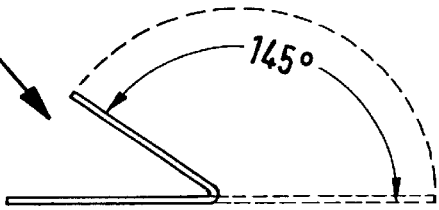

When the plates were bent at room temperature (20° C.) to angles of 10°, 90° and 145° out of the plane of the plates (see FIGS. 8A, B and C, respectively) they showed ductile plastic deformation and retained the desired bending angle after the stress was relieved. It was shown that bending did not change the strength of the plates. Commercial straight 8 hole prior art plates measuring 1.0 mm×5.6 mm×41 mm, part 915-2417, Lot 435600 according to 1.5 mm Lactosorb® System, (manufacturer Walter Lorenz Surgical, Inc., Jaksonville, Fla.) were tested for flexural and thermal properties. The flexural strength of 125 MPa was measured for the plates. The plates were amorphous and showed the glass transition temperature $T_g$ at about 60° C., as measured with DSC (differential scanning calorimetry). When the plates were bent at room temperature (20° C.) to various angles out of the plane of the plates, like in FIG. 8, they showed crazing at relatively small bending angles and fractured in brittle mode when the bending angle exceeded about 10–15°.

Some plates of the invention were placed in a phosphate buffer solution at 0.13 M, pH 7.4, and 37° C. to determine, in vitro, the change in strength over time as the plates degrade. After six weeks the plates were shown to retain more than 80% of their original flexural strength, while the flexural strength was approximately zero at about 18 weeks. The plates were completely absorbed after about two years in vivo.

Bending of prior art plates was also studied in the following way: Pellets of copolymer material comprising about 80 mol-% L-lactide and about 20 mol-% glycolide as described above were placed in a rectangular stainless steel mold measuring 1.2×50×100 mm. The mold was then placed into a vacuum press and evacuated to about 0.02 mbar. The mold was heated to 165° C. (about 10° C. above Tm) and a closing force of 60 kN was applied to the mold or five minutes. The mold was then cooled rapidly (in 2 minutes) to room temperature (20° C.) with cooling water led into cooling channels in the walls of the mold. The mold was opened and the plate-like preform was removed from the mold. Such preforms were then further processed with drilling and grinding producing plates having a configuration similar to the plate shown in FIG. 2B. The dimensions of machined plates were 1.2'5.5×40 mm, and the drillholes were similar to those in the oriented plates. The crystallinity of the plates were determined to be about 5%. To induce crystallinity, some plates were annealed for 16 hours under vacuum (0.02 mbar) at 110° C. After annealing the crystallinity of those plates was about 20%. The plates were then gamma sterilized with a minimum dose of 2.5 MRad (25 kGy). After gamma irradiation the inherent viscosity of the plates was about 1.4 dl/g and the molecular weight Mv was about 47,000. The flexural strength of 115 MPa and 106 MPa was measured for the nonannealed and annealed plates, respectively. When the plates were bent at room, temperature (20° C.) to various angles out of the plane of the plates they showed crazing already at small bending angles between 10–20° and fractured in brittle mode when the bending angle exceeded about 25°.

EXAMPLE 2

A cylindrical rod with a diameter of 6.1±0.2 mm was made of P(L/DL)LA (70/30) (trademark Resomer® LR708 of Boehringer Ingelheim, Ingelheim am Rhein, Germany, with inherent viscosity 5.5 dl/g) by single screw extrusion (with the same extruder as in Example 1). Rods were cooled to the ambient temperature (20° C.).

Extruded rods were oriented (and self-reinforced) by die drawing method (with the draw ratio of 4). Diameter of the drawn rods was 3.0±0.1 mm. Suitable drawing temperatures for the material were between 70–100° C.

About a 150 mm long piece of the oriented, self-reinforced rod was set between two parallel compression molding plates. The rod was preheated three minutes at 60±5° C. between the plates under gentle compression (<1 kN). After preheating the temperature of the compression molding plates was elevated to 90° C. At the same time, the compression force was elevated to 30 kN. The thus made plate (thickness 1.2 mm) was cooled during 2 minutes to the temperature of 50° C. under compression force of 30 kN and released from the mold. The total cycle time was 8 minutes. Such plates were machined mechanically to the final dimensions of 1.2 mm×3 mm×40 mm. The plates were then sterilized with γ-radiation (25 kGy).

Flexural strength of the sterilized oriented, self-reinforced plates was measured at 150±20 MPa. The crystalinity of the plates was 0%, as measured by differential scanning calorimetry (DSC). The amorphous plates were bent in situ (at room temperature) without any preheating to an angle of 90° out of the plane of the plate (with the method illustrated in FIG. 8). The plates showed ductile plastic deformation and retained the desired bending angle after the bending stress was relieved.

In the bending of prior art plates, the following occurred. Nonoriented corresponding plates with dimensions of 1.2 mm×3 mm×40 mm were manufactured of Resomer LR 708 by injection molding (molding machine: Battenfeld injection molding machine molded 230/45 Unilog 2000, Manufacturer: Battenfeld Kunststoffmaschinen Ges M.G.H., Austria). The plates were kept at room temperature (20° C.) for 2 hours before bending them as above. DSC measurements showed that the plates were amorphous, and all plates broke before a bending angle of 90° was achieved.

EXAMPLE 3

Thermoplastic, bioabsorbable pseudo-polyaminoacid poly (DTH carbonate) (PDTHC) ($M_w$=200,000) was synthesized according to S. I. Ertel and J. Kohn, J. Biomed. Mater. Res. 28 (1994) 919–930 and F. H. Silver et al., J. Long-Term Effects Med. Implants 1 (1992) 329–346, the entire disclosure of which is incorporated herein by way of this reference.

Thermoplastic bioabsorbable polyorthoester (POE) ($M_w$=80,000) was synthesized of diketene acetal and of diols trans- cyclohexane dimethanol and of 1,6-hexanediol (60// 40 ratio of diols) according to Daniels, A. U. et al., Trans. Soc. Biomater. 12 (1989) 235 and Daniels, A. U. et al. Trans. Soc. Biomater. 12 (1989) 74, the entire disclosure of which is also incorporated herein by way of this reference.

Thermoplastic, bioabsorbable polyanhydride (PAH) ($M_w$=20,000) was synthesized of 1,3 bis (p-carboxyphenoxy) propane and sebacic acid according to U.S. Pat. No. 5,618,563, Example 1, the entire disclosure of which is also incorporated herein by way of this reference.

Poly-L-lactide (PLLA) ($M_w$=700,000) was supplied by PURAC biochem bv, Gorinchem, Holland.

Each polymer, PDTHC, POE, PAH and PLLA was extruded to cylindrical bars according to Example 1 herein, and they were oriented uniaxially by drawing them through a heated die at a temperature (T) 20° C. above $T_g$ of the corresponding polymer. The draw ratio was in each case 2.5. The uniaxially oriented rods were processed to biaxially oriented plates with the mold compression method of Example 1 herein. Heating was done in each case at $T=T_g+20°$ C., where $T_g$ was the glass transition temperature of the corresponding polymer. The plate preforms were machined with grinding to plates with dimensions of 1.2 mm×5.5 mm×40 mm.

Corresponding non-oriented plates were prepared by melt extrusion from the same polymers to compare the bending behavior of oriented and non-oriented plates. Each polymer melt was extruded through a die with a rectangular outlet with dimensions 1.5 mm×20 mm. The melted polymer preform was led from the die outlet onto a cooling belt where it solidified forming a non-oriented plate-preform with the thickness of 1.2 mm. After the preforms were-cooled to room temperature they were processed mechanically to plates with the same dimensions as the oriented plates.

The oriented and non-oriented plates were bent at room temperatured to an angle of 45° C. by the method of Example 1 (FIG. 8) herein. All the oriented plates were bent without significant damage of the bending area and retained their bent form after the bending stress was released. Non-oriented PLLA, POE and PAH plates broke during bending and non-oriented PDTHC plates developed many cracks and crazes, to the bending area. The oriented plates were redeformed without significant damage by bending them again at room temperature to their original configurations. The non-oriented, bended PDTHC plates either broke or damaged further when bent back to their original configurations at room temperature.

The tensile strength of redeformed (straight) oriented plates was 80–95% of the tensile strength of oriented plates that had never been bent. The tensile strength of non-oriented, non-broken, redeformed PDTHC plates was ca. 20–40% of the tensile strength of corresponding plates that had never been bent. This experiment showed that oriented plates can be bent and rebent at room temperature, but non-oriented plates do not bear up to such a treatment.

EXAMPLE 4

A rectangular bar with the thickness of 2.4 mm and the width of 3 mm was made of P(L/DL)LA (70/30) by melt extrusion according to Example 2.

The non-oriented billet was oriented uniaxially in hydrostatic extrusion according to FIG. 9. A 10 cm long billet 40 was located into the chamber 41 of a hydrostatic extrusion device 42 which chamber 41 was filled with silicone oil 43. At the tip of the device 42 was a stainless steel die 44 with the rectangular, conical inner channel 45 with the inlet dimensions of 2.4 mm×3 mm outlet dimensions of 1.2 mm×3 mm and channel length of 10 mm. The tip 46 of the billet 40 was first cut conically and the tip 46 was pushed tightly into the channel 45 of the die before filling the chamber with silicone oil 43 and beginning with the hydrobstatic extrusion.

Figures 9A, 9B, 9C:
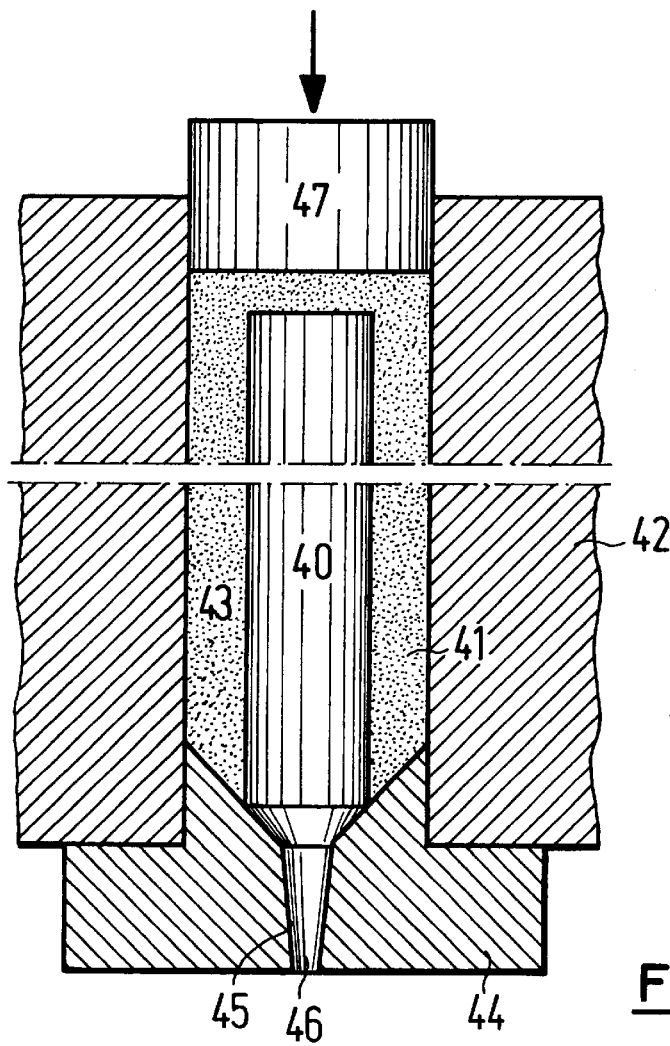
FIG. 9A is a schematic cross-sectional view of a hydrostatic extruder for orientation of bioabsorbable, polymer billets.
FIGS. 9B and 9C show schematically the change of cross-section of a rectangular billet during hydrostatic extrusion.

The chamber 41, die 44, oil 43 and billet 40 were heated to the hydrostatic extrusion temperature of 70° C., and the system was kept at this temperature 30 min before starting the hydrostatic extrusion process. The process was started by increasing the hydrostatic pressure of silicone oil 43 inside of the extrusion chamber 41 to 150 MPa with a hydraulic piston 47. The hydrostatic pressure forced the billet through the die, so that the material was oriented uniaxially when the cross-section of the rectangular billet changed from 2.4 mm×3 mm (FIG. 9B) to 1.2 mm×3 mm (FIG. 9C). The oriented preform was wiped clean with soft paper and cut to plates with dimensions of 1.2 mm×3 mm×40 mm.

An in situ bending test of the plates was done at room temperature as in Example 2. The plates showed ductile plastic deformation at room temperature and retained the bending angle of 90° after the bending stress was relieved.

EXAMPLE 5

Rectangular bars were manufactured of P(L/DL) LA (70/30) with melt extrusion according to Example 2, but this time mixing of the P(L/DL)LA (70/30) powder before extrusion was carried out with 20 wt-% of bioactive glass (BAG) particles. Composition of the bioactive glass was: $Na_2O$ (6 wt-%), $K_2O$ (12 wt-%), $M_gO$ (5 wt-%), CaO (20 wt-%), $P_2O_5$ (4 wt-%) and $SiO_2$ (53 wt-%), The glass was manufactured according to WO 96/21638, the entire disclosure of which is incorporated herein by way of this reference. A particle fraction with sizes between 20 μm–60 μm was sieved from crushed glass and this faction was used as a bioactive particle filler in the P(L/DL)LA.

The melt extruded P(L/DL)LA bars with 20 wt-% of BAG particle filler were oriented with hydrostatic extrusion according to Example 4, but using a processing temperature of 90° C. and hydrostatic pressure of 200 MPa. The oriented billets were processed to bending test plates as in Example 4. Also, these plates showed ductile plastic deformation without breaking at room temperature when bent to a bending angle of 90° and the plates retained their blended configuration after the bending stress was relieved.

Corresponding non-oriented plates were prepared by melt extrusion from P(L/DL)LA and 20 wt-% of BAG particles with the equipment and process described in Example 2. All the non-oriented plates broke during the bending experiment (which was done according to Example 4) before reaching the bending angle of 90°.

EXAMPLE 6

Similar bars as in Example 5 were manufactured from P(L/DL)LA, but using as filler, instead of bioactive glass particles, bioactive glass fibers which were melt spun from the same glass raw material. The fibers had diameters between 40–80 μm and the fibers were cut to 6 mm long particles before mixing them with P(L/DL)LA powder.

The mixture ratio 80 wt-% of P(L/DL)LA and 20 wt-% of bioactive glass fibers was used. The melt extrusion and orientation of the melt extruded billets with hydrostatic extrusion, and also the plate manufacturing and plate testing, were done as in Example 5. The oriented plates with bioactive glass fiber reinforcement also showed ductile plastic deformation without breaking at room temperature when bent to a bending angle of 90°, and the plates substantially retained their bent configuration after the bending stress was Corresponding non-oriented plates were prepared by melt extrusion from P(L/DL)LA and 20 wt-% of bioactive glass fibers with the equipment and the process described in Example 2. All the non-oriented plates broke during the bending experiment (which was done according to Example 4) before reaching the bending angle of 90°.

EXAMPLE 7

Figure 10A:
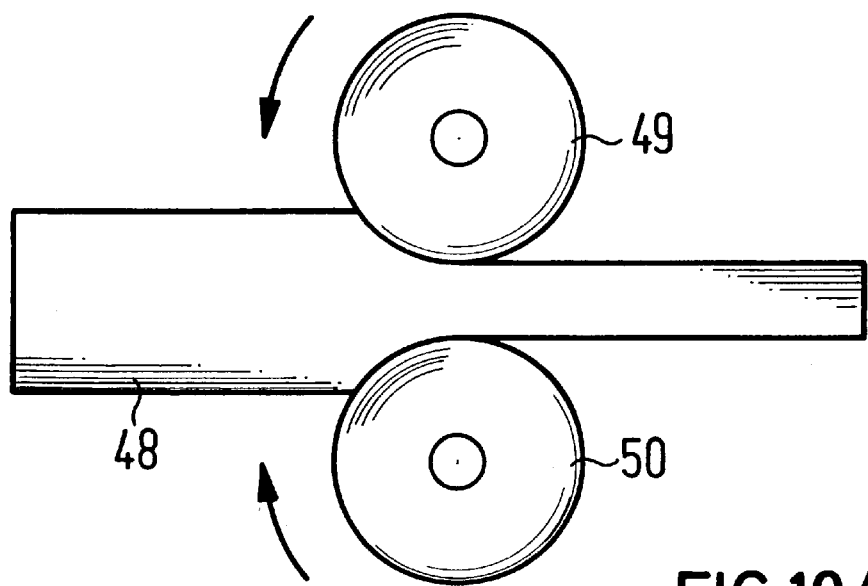
FIGS. 10A and 10B show schematically a roller system for deformation and, orientation of plate preforms.
Figure 10B:
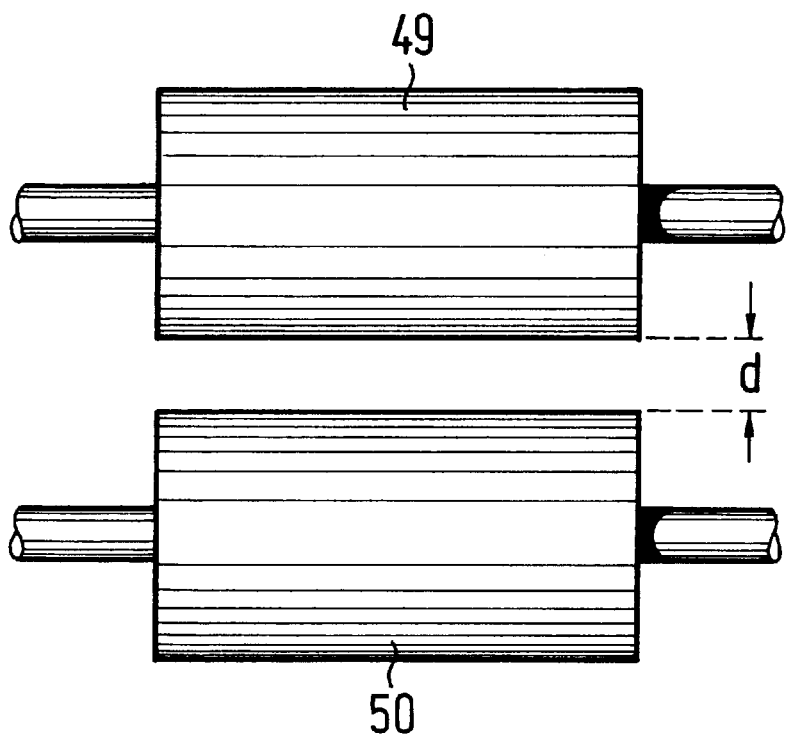

Non-oriented, rectangular bars with cross-sectional dimensions of 2 mm×3 mm were prepared by melt-extrusion (with single screw extruder Axon) from polymers PDTHC, POE and PLLA described in Example 3. Each bar 48 was deformed and oriented biaxially by drawing-rolling technique, by drawing each bar slowly (drawing speed 1 cm/min) through heated rollers (49 and 50) in a manner shown in the schematic side-view in FIG. 10A. As is shown in the frontal view in FIG. 10B, the minimum distance d between the rollers (49 and 50) determined the final thickness of the rolled-drawn billets. The value of d=1.1 mm was used in these experiments. The temperature of the rollers was $T_g+30°$ C., where $T_g$ was the glass transition temperature of the corresponding polymer.

The oriented rolled-drawn preforms were processed into plates with dimensions 1.1 mm×4 mm×40 mm by mechanical machining (grinding). The deformability of such plates was tested at room temperature with the bending experiment described in Example 2. All the plates could be bent to an angle of 90° without significant damage. The plates also retained the bent configuration immediately after releasing the bending force.

EXAMPLE 8

The objective of the bioabsorbable cranial, facial, mandibular or maxillar plating system is to provide adequate fixation of the osteotomies made or fractures treated during the healing process. To fulfill this demand, the plates must be located in close contact with the attached bone throughout the surface of the plate to provide maximum fixation. Depending on the anatomical conditions, the demand for bending or twisting is variable as per the location of the plate and/or the physical characteristics of the bone surface of each individual patient.

In the mandible, the angulus area requires twisting of the plates in a propeller form with axial torsion angles of up to 90 degrees; as in the apical region, the plate must be curved with a radius of 40 to 60 mm to follow the congruence of the bone surface. In the maxilla, the plates must be bent in a step-like or curved form of up to 90 degrees of angulation. In most cases, a combination of bending, curving and twisting is used to achieve exactness of contact.

The following clinical experiments demonstrated, that changes in the form of the plates are stable for the purposes of surgical bone fracture fixation operations, once plates are bent at room temperature to be flush with the bone surfaces to be fixed.

Mandibular symphysis fractures (like 10 in FIG. 1) of ten patients were treated with oriented six-hole P(L/DL)LA plates (see 6 in FIG. 1) with dimensions 1.2 mm×4 mm (made according to Example 2), using P(L/DL)LA screws (diam. 2.0 mm, length 8 mm) for plate fixation. The straight plates were bent, in situ during the operation to the curved form to be flush on the bone surface. An uneventful, good healing of all fractures was seen after one year's follow up.

Mandibular angular fractures in 6 patients were treated with six hole plates made of oriented PDTHC of Example 3. The plates had dimensions of 1.2 mm×5.5 mm×40 mm and they were twisted into a propeller form at room temperature to be flush with the bone surface. The twisted plates were fixed on bone over the fracture with PDTHC screws (2.0 mm diam., 8 mm length). All fixations retained their position with uneventful, good healing as was seen after 6 months follow-up.

What is claimed is:

1. A method of deforming an ostoesynthesis plate into a desired shape comprising:
   providing an oriented osteosynthesis plate that is fabricated from a uniaxially or biaxially oriented polymer;
   exposing the osteosynthesis plate to a temperature that is below the glass transition temperature of the osteosynthesis plate; and
   deforming the osteosynthesis plate into a desired shape at the temperature that is below the glass transition temperature of the osteosynthesis plate, wherein the osteosynthesis plate is capable of maintaining the desired shape at the temperature that is below the glass transition temperature of the osteosynthesis plate.

2. The method of claim 1, wherein the temperature that is below the glass transition temperature is room temperature.

3. The method of claim 1, wherein the osteosynthesis plate is deformable along three mutually perpendicular axes.

4. A method for stabilizing at least two bone portions comprising:
   providing an osteosynthesis plate that is fabricated from a uniaxially or biaxially oriented polymer;
   deforming into a desired shape the osteosynthesis plate at a first temperature that is below the glass transition temperature of the osteosynthesis plate, wherein the osteosynthesis plate is capable of maintaining the desired shape at the temperature that is below the glass transition temperature of the osteosynthesis plate;
   securing the osteosynthesis plate to the at least two bone portions; and
   stabilizing the at least two bone portions.

5. The method of claim 4, further comprising maintaining the desired shape of the osteosynthesis plate at a second temperature that is different than the first temperature.

6. The method of claim 5, wherein the second temperature is body temperature.

7. The method of claim 4, wherein the first temperature is room temperature.

8. The method of claim 4, further comprising allowing resorption of the osteosynthesis plate after the at least two bone portions are stabilized.

9. The method of claim 8, wherein after the at least two bone portions are stabilized comprises after the at least two bone portions have ossified together.

10. The method of claim 8, wherein after the at least two bone portions are stabilized comprises after a fracture between the at least two bone portions has healed.

11. The method of claim 4, wherein the at least two bone portions comprises a plurality of bone portions.

12. The method of claim 4, wherein the osteosynthesis plate comprises an elongate section defining at least two fastener openings.

13. The method of claim 12, wherein the at least two fastener openings comprises a plurality of fastener openings.

14. The method of claims 4, further comprising forming additional fastener openings in the elongate section.

* * * * *

UNITED STATES PATENT AND TRADEMARK OFFICE
CERTIFICATE OF CORRECTION

PATENT NO. : 6,692,497 B1
DATED : February 17, 2004
INVENTOR(S) : Törmälä et al.

It is certified that error appears in the above-identified patent and that said Letters Patent is hereby corrected as shown below:

Column 1,
Line 26, change "discloser" to -- disclosure --;
Line 58, change "discloures" to -- disclosure --;

Column 2,
Line 50, change "60º C.)." to -- 60º C). --;

Column 3,
Line 18, change "repecitive" to -- respective --;

Column 4,
Lines 46, 49, 55, 58 and 62, change "an" to -- a --;

Column 5,
Lines 3 and 38, change "an" to -- a --;

Column 6,
Lne 17, change "an" to -- a --;

Column 10,
Line 9, change "makeing" to -- making --;
Line 10, change "to be" to --      --;
Line 24, change "due to smaller" to -- due to a smaller --;
Line 43, change "sa" to --      --;

Column 11,
Line 44, change "off" to -- of --;
Line 50, change "Vainionpääet al." to -- Vainionpää et al. --;

Column 12,
Line 22, change "antibiotics chemotherapeutic" to -- antibiotics, chemotherapeutic --;
Line 45, change "with. uni- and/or" to -- with a uni- and/or --
Line 46, change "process, to" to -- proccess to --;

Column 13,
Line 20, change "others" to -- other --

UNITED STATES PATENT AND TRADEMARK OFFICE
CERTIFICATE OF CORRECTION

PATENT NO. : 6,692,497 B1
DATED : February 17, 2004
INVENTOR(S) : Törmälä et al.

It is certified that error appears in the above-identified patent and that said Letters Patent is hereby corrected as shown below:

Column 14,
Line 24, change "closing the package" to -- closing the package. --
Line 47, change "no" to -- not -- ;
Line 56, change "archived" to -- achieved --;

Column 15,
Line 61, change "pre-heating the" to -- pre-heating, the --;

Column 16,
Line 54, change "$1.2^15.5\text{x}40$" to -- 1.2x5.5x40 --;

Column 19,
Line 63, change "stress was" to -- stress was relieved --;

Column 22,
Line 29, change "claims" to -- claim --;

Signed and Sealed this

Twelfth Day of October, 2004

JON W. DUDAS
*Director of the United States Patent and Trademark Office*